US007427358B2

(12) United States Patent
Villanova et al.

(10) Patent No.: US 7,427,358 B2
(45) Date of Patent: Sep. 23, 2008

(54) PROCESS FOR THE RECOVERY OF TYROSOL AND HYDROXYTYROSOL FROM OIL MILL WASTEWATERS AND CATALYTIC OXIDATION METHOD IN ORDER TO CONVERT TYROSOL IN HYDROXYTYROSOL

(75) Inventors: Luigi Villanova, Zollino (IT); Luciano Villanova, Zollino (IT); Gianluca Fasiello, Zollino (IT); Alessandro Merendino, Zollino (IT)

(73) Assignee: Lachifarma s.r.l. Laboratorio Chimico Farmaceutico Salentino, Zollino (IT)

( * ) Notice: Subject to any disclaimer, the term of this patent is extended or adjusted under 35 U.S.C. 154(b) by 495 days.

(21) Appl. No.: 11/197,359

(22) Filed: Aug. 5, 2005

(65) Prior Publication Data
US 2006/0070953 A1  Apr. 6, 2006

(30) Foreign Application Priority Data
Aug. 6, 2004  (IT)  .................. MI2004A1627

(51) Int. Cl.
*B01D 61/00* (2006.01)
*B01D 63/00* (2006.01)
*B01D 15/08* (2006.01)
*B01D 11/00* (2006.01)
*B01D 71/00* (2006.01)

(52) U.S. Cl. ............ 210/634; 210/635; 210/638; 210/644; 210/649; 210/650; 210/652; 210/653; 210/656

(58) Field of Classification Search .............. None
See application file for complete search history.

(56) References Cited

U.S. PATENT DOCUMENTS

| 6,454,946 | B1* | 9/2002 | DeFrees | 210/653 |
|---|---|---|---|---|
| 6,936,173 | B2* | 8/2005 | DeFrees | 210/653 |
| 7,282,150 | B2* | 10/2007 | Kuriki et al. | 210/634 |
| 2003/0029799 | A1* | 2/2003 | DeFrees | 210/652 |
| 2003/0125573 | A1* | 7/2003 | Millis et al. | 549/411 |
| 2003/0144562 | A1* | 7/2003 | Afzali-Ardakani et al. | 570/212 |
| 2005/0103711 | A1* | 5/2005 | Emmons et al. | 210/639 |
| 2005/0269265 | A1* | 12/2005 | DeFrees | 210/639 |

* cited by examiner

*Primary Examiner*—Krishnan S Menon
(74) *Attorney, Agent, or Firm*—Young & Thompson

(57) ABSTRACT

A for preparing Tyrosol and/or Hydroxytyrosol from oil mill wastewaters.
includes:
a) Microfiltration (MF), Ultrafiltration (UF). Nanofiltration (NF) and Reverse Osmosis (RO) of the OMW;
b) Separation of Tyrosol, Hydroxytyrosol and other phenolic compounds from the concentrated RO;
c) Oxidation of the obtained Tyrosol to Hydroxytyrosol in the presence of methyl rhenium trioxide and of hydrogen peroxide in a protic solvent.

15 Claims, 5 Drawing Sheets

PROCESS FOR THE RECOVERY OF TYROSOL AND HYDROXYTYROSOL FROM OIL MILL WASTEWATERS AND CATALYTIC OXIDATION METHOD IN ORDER TO CONVERT TYROSOL IN HYDROXYTYROSOL

This invention concerns a process for the recovery of Tyrosol and Hydroxytyrosol from the oil mill wastewaters and a method of catalytic oxidization of Tyrosol to Hydroxytyrosol.

BACKGROUND OF THE INVENTION

The problem of the oil mill wastewaters is well known. The olives pressing in the oil productive countries creates as by-product, at the rate of 40/50% of the weight of the pressed olives, oil mill wastewaters rich in highly polluting organic compounds (polyphenols) which create a number of environment and ecological problems connected with their elimination and treatment.

Many methods have been proposed to eliminate this kind of problem, for example by a technique of photo catalysis, ozonization, etc., but up to today no satisfying solution is available yet, in particular a solution which does not involve a drastic contraction of production with a strong increase of prices.

On the other hand, it is known that the oil mill wastewaters contains metabolites of interest for the cosmetic, pharmaceutical, dietetic and food industry. The isolation of these metabolites, especially Tyrosol and Hydroxytyrosol, from the oil mill wastewaters, is therefore an aim of particular applied interest, thanks to their antioxidant properties.

For example, WO2004/005228 describes an extraction process of Hydroxytyrosol, comprising the acidification of the oil mill wastewaters followed by extractions by organic solvents and supercritical fluids.

DESCRIPTION OF THE INVENTION

It has now been found a process for the treatment of the oil mill wastewaters (OMW) allowing on the one hand the detoxification of the OMW with a recovery of water up to 85% for well-watered and civil use as by law enacted and, on the other hand, a recovery of highly pure Tyrosol and Hydroxytyrosol.

Besides, this invention provides a process for the subsequent catalytic oxidation of Tyrosol into Hydroxytyrosol.

This process allows the recovery of every starting-liquid component, the re-use and the exploitation of every single separated component.

The process of the invention is easily industrially applicable with no additional costs influencing the olive oil selling price and it gives the possibility to market products based on Hydroxytyrosol, which can be used for human health (medicines), for the health care (integrators, nutraceuticals, cosmetics) and for food industries.

The process of the invention includes:
- Rough Filtration (RF), Microfiltration (MF), Ultrafiltration (UF), Nanofiltration (NF) and Reverse Osmosis (RO) of the OMW;
- Chromatographic separation of Tyrosol, Hydroxytyrosol and other phenolic compounds from the concentrated RO;
- Oxidation of the obtained Tyrosol to Hydroxytyrosol in the presence of methyl rhenium trioxide and of hydrogen peroxide in a protic solvent;
- Concentration and pulverization of the high molecular weight portion with the recovery of water and compounds with a high added value.

The sequential stages of Rough Filtration, Microfiltration, Ultrafiltration, Nanofiltration and Reverse Osmosis, schematized in FIG. 1 referring to specified intervals of molecular dimension, allow to recover, after concentration, at least 1 g/l of Hydroxytyrosol and 0.6 g/l of Tyrosol.

These components can be then isolated with purity higher than 98% by chromatography in inverted phase on a preparatory column.

The preparatory column is preferably filled with a macroporous co-polymer of divinylbenzene and N-vinylpyrrolidone. This co-polymer, thanks to the polar functional group, is able to retain the polar molecules. The use of columns filled with this co-polymer allows isolating the components (Tyrosol, Hydroxytyrosol, tri-hydroxybenzoic acid, Catechol, etc.) contained in the mixture and in particular to prepare Hydroxytyrosol with a high level of purity free from Catechol (ortho-diphenol contained in the OMW and toxic for humans).

The concentration ratio (food/extract) in the stages of Microfiltration, Ultrafiltration, Nanofiltration and Inverse Osmosis is preferably higher than 8.

The invention process allows to recover at least 70% of the water volume as to the starting total volume of the OMW, with such a quality that it is possible to keep within the limits defined by the present laws about the possible agricultural/civil use (lower than 100 $mgO_2/l$ of COD). Preferably, the stages of Ultrafiltration, Nanofiltration and Inverse Osmosis are carried out at neutral or alkaline pH.

A further treatment of evaporation/condensation on the concentrates of the different stages of filtration allows to recover about 15% further, up to a total 85% recovery of water.

The fraction of organic material recovered from the previous stages of membrane before Inverted Osmosis consists of polyphenolic compounds distributed in various classes of molecular weight.

These polyphenols, even if remarkably variable in the single units composition, possess anti-oxidant activity and free radicals scavenger activity typical of Hydroxytyrosol (Phenolic function sterically blocked, catecholic function etc.). Moreover, these polyphenols possess characteristic rheological properties (resistance, stability, presence of polar functional groups) that make them interesting materials for a number of applications in material science, some of which will be mentioned later. As to anti oxidant properties, it is widely documented the possibility to use polyphenols as anti-oxidants to protect plastic materials (polyethylene with high and low density, polystyrene etc.) from oxidative photodegradation that determines a rapid increase of their fragility [Composite Films Based on Waste Gelatine: Thermal-Mechanical Properties and Biodegradation Testing; Chiellini E., et al.; Polym. Degrad. Stabil., 2001, 73, 549-555]. Besides, because of polyphenols highly chelant properties, these can be used as additive for fodder industry, as carrier of metal ions useful in the diet and as antioxidants. The use of polyphenols in food preservation is also a potential application. These polyphenols can be also used to treat natural fibres to confer new mechanical and physical characteristics, among which an improved resistance to photo-oxidation, an increase of lengthwise resistance and a significant modification of gas absorption characteristics, like for example carbon dioxide (particularly useful for preparing filters from fibres to purify air) [Esterification of cellulose-Enriched Agricultural By-Products and Characterisation of Mechanical Properties of Cellulosic Films; Chavelon G. et al.; Carbohyd. Polym. 2000, 42, 385-392]. A further application of these polyphenols consists in exploiting their tensioactive properties as natural components in the field of cosmetics (for example in the formulation of soft soaps, bath-salts, aspersion powders comprising exclusively natural components, for example for infant care).

Polyphenols obtained by this process can be used for cosmetic and pharmaceutical preparations for the prevention of oxidative stress on the dermal membrane such as anti-aging, but also for the skin fading as antagonists of the melanogenesis process.

Whereas fractions, which contain antioxidant scavenger mixtures, eliminate free radicals contained in the melanin structure producing an effect of skin fading, the Tyrosol mechanism of action acts by competing with Tyrosine in the process controlled by an enzyme called Tyrosinase, which constitutes only one part of the total process of melanogenesis. In fact, even Tyrosol is subjected to the enzymatic activity of the Tyrosinase, changing in Hydroxytyrosol according to the scheme 1. It thus competes with the Tyrosine in the enzymatic reaction.

Scheme 1

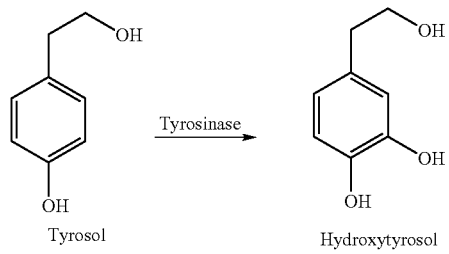

Tyrosol → Tyrosinase → Hydroxytyrosol

Therefore Tyrosol delivered to the deeper derma layers can compete with Tyrosine for tyrosinases reducing the quantity of Dopamine available to continue melanogenesis process, reducing therefore dermal colouring.

The various fractions and compounds such as Tyrosol, Hydroxytyrosol, etc., obtained by the innovative process here described, have been used for the formulation of preparations for topical use to oppose melanogenesis process and induce derma de-colouring and de-pigmenting.

Uses of polyphenols are not limited to the mentioned examples but also include preparation of varnishes, adhesives and composites.

The oxidation reaction of Tyrosol to Hydroxytyrosol can take place in the homogeneous, heterogeneous or transition phase, using water and hydrocarbonated solvents such as pentane, heptane and similar.

The catalyst methylrhenium trioxide (MTO) can also be used in a form bound to inert polymeric matrixes such as poly(4-vinylpyridine) and polystyrene. In this case, the heterogeneous catalyst used for the oxidation can be recovered from the reaction system by the simple filtration and re-used in at least ten sequential cycles of transformation without visible loss of activity and selectivity.

Anyhow, conditions of homogeneous catalysis are preferred for the oxidation, using protic solvents such as water, alcohols $C_1$-$C_3$, acetic acid or mixtures thereof.

The oxidation process of the invention can obviously be performed on Tyrosol not derived from the method for the treatment of the oil mill wastewaters but from other sources too, for example commercial Tyrosol of technical grade.

The invention will now be illustrated in more details in the following examples.

EXAMPLE 1

Combined Treatment of OMW by Process of Micro, Nano, Ultrafiltration, Inverse Osmosis and Techniques of Separation and Recovery FIG. 1 is a diagram of the main component of the extract obtained by the different fractions.

The pilot-plant has been provided by the firm Hydro Air Research according to the Applicant's project and consists of three units.

The first unit consists of 7 rough filtration modules installed in the sequence described here below:

| Module | Light (mm) | Light (mesh) |
| --- | --- | --- |
| 1 | 4.76 | 4.57 |
| 2 | 1.07 | 18.28 |
| 3 | 0.396 | 45.71 |
| 4 | 0.188 | 91.43 |
| 5 | 0.089 | 182.87 |
| 6 | 0.055 | 274 |
| 7 | 0.033 | 400 |

The second unit consists of 2 modules for microfiltration (MF; 120 000 D; 0.24 sqm×2).

The third unit consists of 4 different modules, which can be used one by one.

| Module | | Surface ($m^2$) | Range (Dalton) |
| --- | --- | --- | --- |
| Ultrafiltration 1 | UF1 | 1.6 | 120000-20000 |
| Ultrafiltration 2 | UF2 | 1.6 | 20000-1000 |
| Nanofiltration | NF | 2.5 | 1000-350 |
| Reverse Osmosis | RO | 2.5 | 350 |

Several tests have been done mainly changing the concentration ratio between the permeated and the extract. In the inverse osmosis step, it is necessary to set the concentration ratio between the extract and the permeated. The exercise temperature should not be over 80° C. for the membrane functionality, but preferably less than 60° C. to protect the metabolites integrity.

Figure 1:
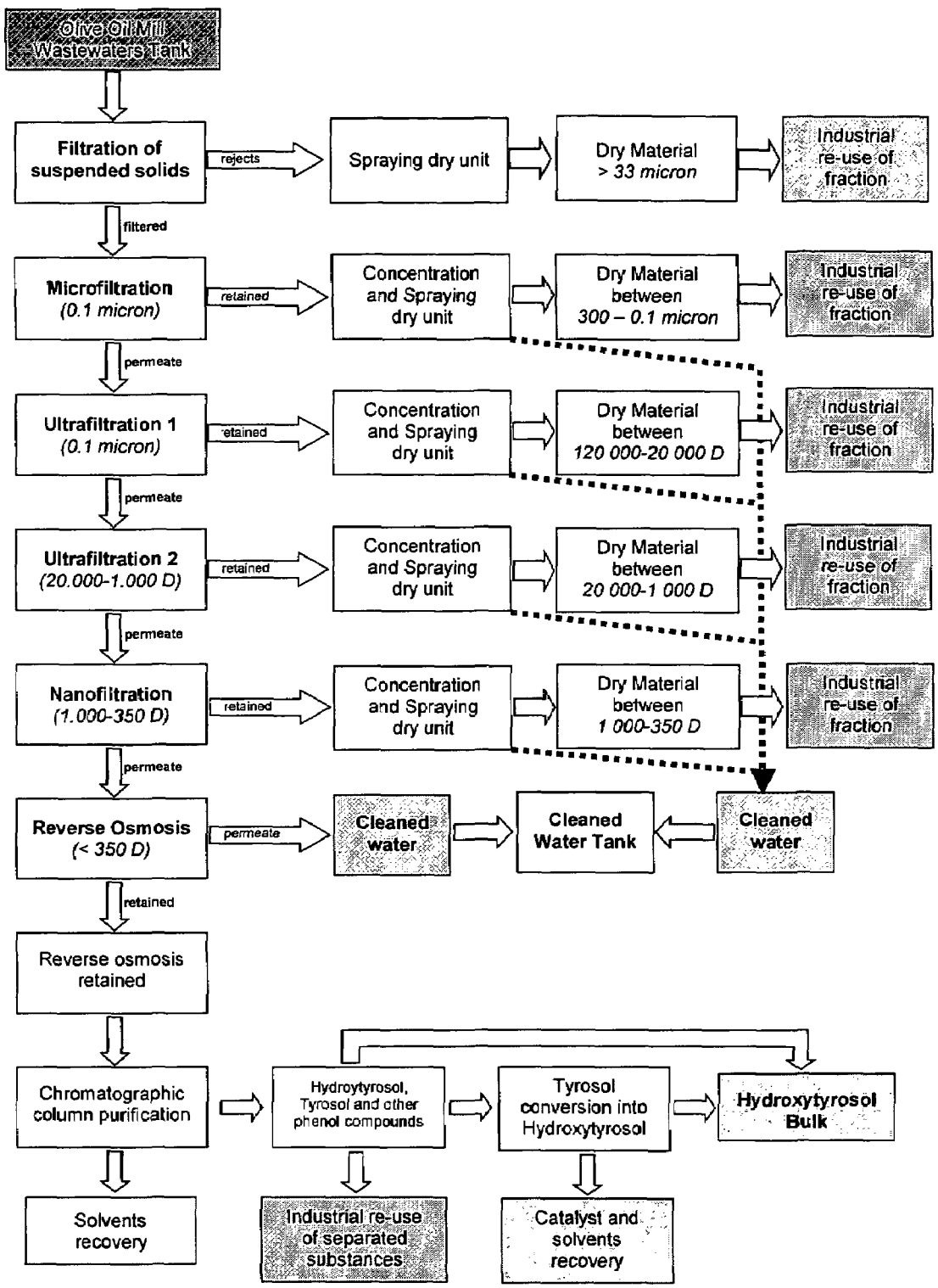

The extract obtained by the different fractions has been characterized in its main components (see FIG. 1). The following scheme shows the concentration values of the most important components, Tyrosol and Hydroxytyrosol.

TABLE 1

Results of the process tests expressed as Tyrosol and Hydroxytyrosol recovered in the osmosis extract.

| | Concentration (g/l) | |
|---|---|---|
| | OH-Tyrosol | Tyrosol |
| Test A | 1.55 | 0.79 |
| Test B | 1.26 | 0.815 |
| Test C | 1.173 | 0.665 |
| Test D | 1.204 | 0.687 |

It may be noted that, according to the described process, developed by the Applicant, the osmosis extract contains more than 1 g/l of Hydroxytyrosol and more than 0.6 g/l of Tyrosol.

Figure 2:
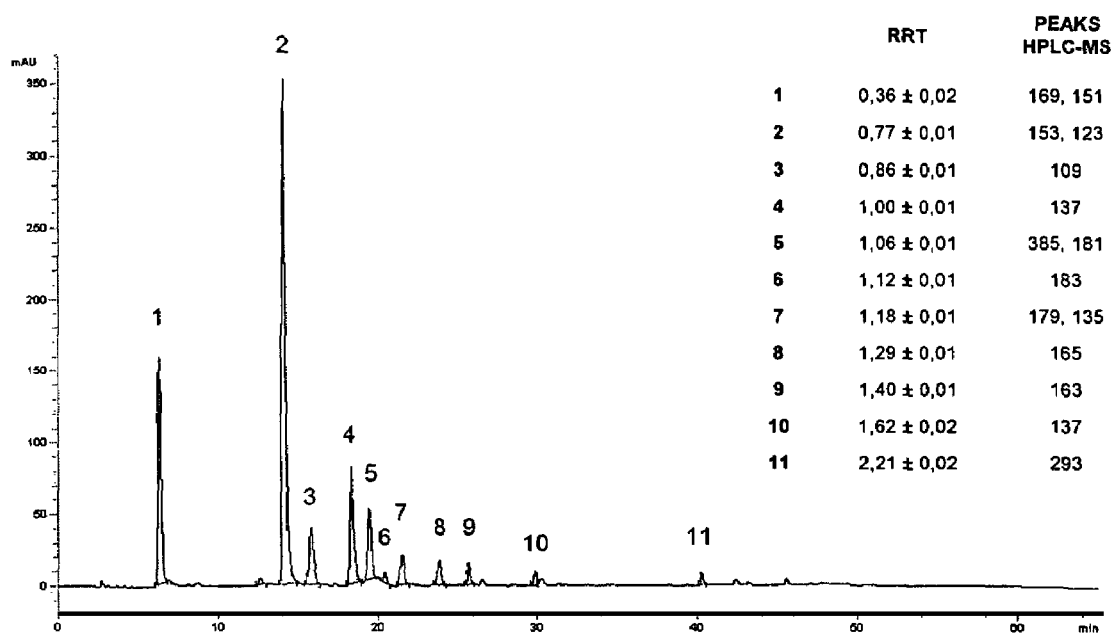
FIGS. 2 and 3 are graphs showing concentration fractions obtained by the different steps of filtration by measuring the macro-descriptive parameters with respectively spectroscopic (FIG. 2) and spectrometric methods (FIG. 3).

The chromatogram HPLC-MS of the inverse osmosis fraction, reported in FIG. 2, shows the peaks area higher than 1%.

The purification of the raw material obtained by flash-chromatography or chromatography on the divinylbenzene/N-vinylpyrrolidone co-polymer allowed the isolation of:

Tyrosol with yield higher than 84% (purity>80%);

Hydroxytyrosol with yield higher than 80% (purity>80%).

The so obtained Hydroxytyrosol and Tyrosol have been brought to purity higher than 98% by semi-preparative HPLC column in inverted phase as, for example, C18 Zorbax® type from Agilent™.

Figure 3:
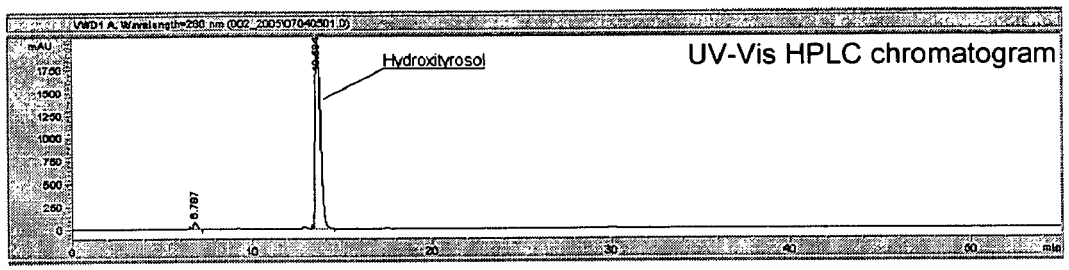
Figure 3:
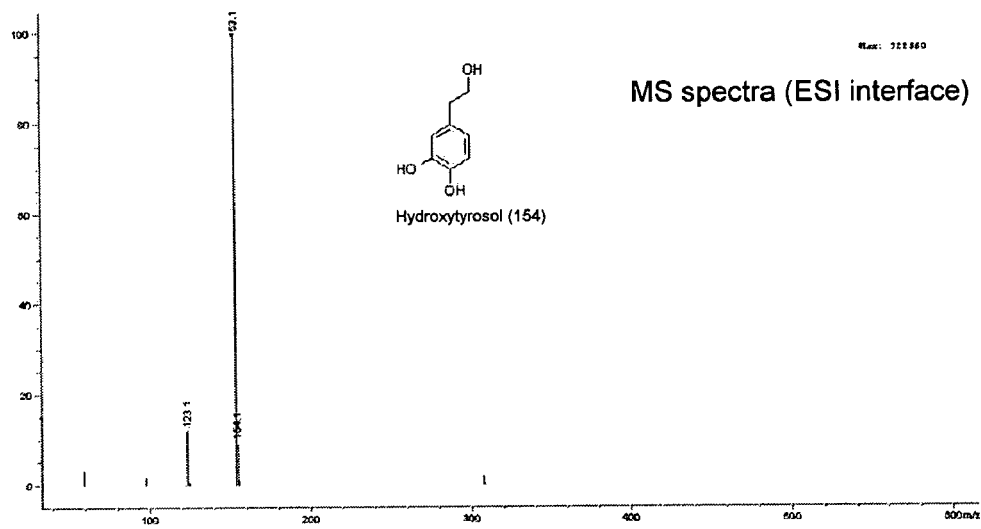
Figure 3:
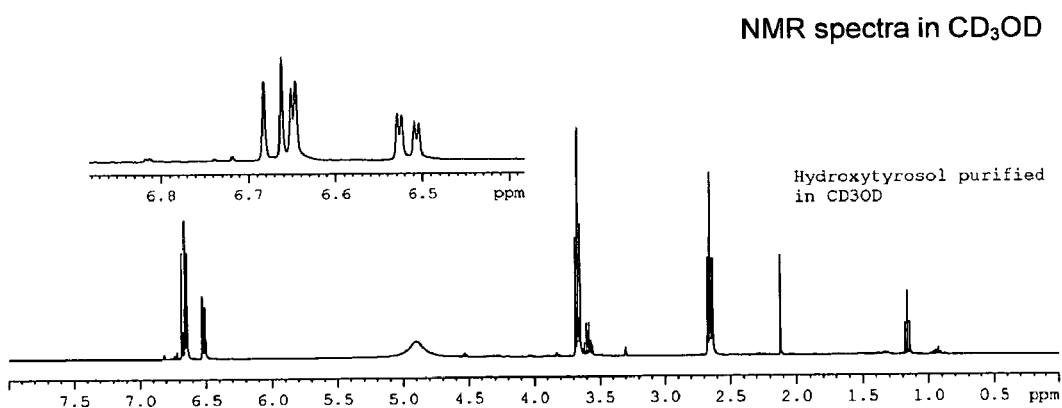

The products obtained by purification have been fully characterised by spectroscopic ($^1$H and $^{13}$C NMR, FT-IR) and spectrometric techniques (GC-MS, LC-MS) and evidence purity higher than 98% (FIG. 3).

Concentration fractions obtained from the different steps of filtration, as described above, have been characterised measuring the macro-descriptive parameters with spectroscopic and spectrometric methods (FIG. 2).

Even if the oil mill wastewaters composition is influenced by various parameters (environmental, varietal, climatic and due to processing), the average values determined for some macro-descriptive parameters on various samples from firms operating in the Salento area is reported below.

TABLE 2

Results of macro-descriptive parameters obtained from characterisation tests of different molecular weight fractions, obtained as described above

| | Lyophilised weight (g/l) | Density (g/ml) | Water % content | Refraction index | Rotation strength | Characteristic peak high @ 277 nm |
|---|---|---|---|---|---|---|
| OMW | 18.44 ± 1.24* | 1.008 ± 0.001 | 98.2 | 1.337 ± 0.001 | 0 ± 0 | 0.05 |
| MF-C | ND | 1.009 ± 0.001 | ND | 1.346 ± 0.001 | 0 ± 0 | 0.01 |
| UF1-C | 32.48 ± 1.38* | 1.012 ± 0.001 | 96.8 | 1.338 ± 0.001 | 0 ± 0 | 0.03 |
| UF2-C | 15.32 ± 1.68* | 1.004 ± 0.001 | 98.5 | 1.334 ± 0.001 | 0 ± 0 | 0.05 |
| NF-C | 61.8 ± 1.95* | 1.028 ± 0.001 | 93.9 | 1.333 ± 0.001 | 0 ± 0 | 0.01 |
| RO-C | 24.52 ± 1.38* | 1.012 ± 0.001 | 97.6 | 1.337 ± 0.001 | 0 ± 0 | 0.22 |

| | Proteins[1] (g/l) | ODF[2] (g/l) | Hydroxytyrosol (g/l) | Tyrosol (g/l) |
|---|---|---|---|---|
| OMW | ND | 2.84 ± 0.09 | 0.26 ± 0.02 | 0.08 ± 0.01 |
| MF-C | 1.5 ± 0.2 | 4.06 ± 0.63 | ND | ND |
| UF1-C | 0.1 ± 0.1 | 4.04 ± 0.57 | ND | ND |
| UF2-C | >0.1 | 2.00 ± 0.15 | 0.12 ± 0.07 | 0.13 ± 0.05 |
| NF-C | 0.2 ± 0.1 | 4.69 ± 0.50 | 0.29 ± 0.05 | 0.22 ± 0.06 |
| RO-C | 0.1 ± 0.1 | 7.81 ± 2.53 | 1.41 ± 0.21 | 0.81 ± 0.03 |

ND = Not Determined

*Significant differences ANOVA ($p < 0.05$) and DUNCAN ($p < 0.05$)

[1]Proteins expressed as lactoalbumin equivalents

[2]Orthodiphenols expressed as chlorogenic acids equivalents

EXAMPLE 2

Tyrosol Catalytic Oxidation to Hydroxytyrosol in Homogeneous and Heterogeneous Conditions Different reactions have been performed (Scheme 2) and their results are resumed in Table 3.

Scheme 2

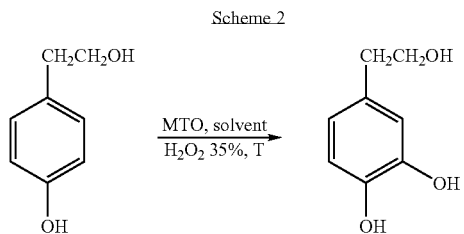

As a general procedure, all reactions have been performed on one gram of Tyrosol in the solvent (5 ml) at the indicated temperature (see table) being present 10% of weight of MTO and an excess of $H_2O_2$ (about 2.5 equivalents). Reactions were treated with EtOAc extraction. Organic extracts were dried on anhydrous sodium sulphate and evaporated in a Rotavapor® at reduced pressure. The raw reaction material was purified by flash-chromatography.

TABLE 3

Results of the homogeneous oxidation of Tyrosol to Hydroxytyrosol

| Catalyst | Solvents | Temperature °C. | Conversion % | Yield (a) % |
|---|---|---|---|---|
| MTO | EtOH | 20 | 25 | 100 |
| MTO | EtOH | 45 | 86 | 20 |
| MTO | $CH_3COOH$ | 20 | 0 | 0 |
| MTO | $CH_3COOH$ | 45 | 55 | 28 |
| MTO | $H_2O$ | 20 | 42 | 35 |
| MTO | $H_2O$ | 45 | 50 | 75 |

(a) Yields are expressed in percentage of conversed.

The best results have been obtained with MTO (10% of weight compared to the substratum) working in EtOH at 20° C. and in $H_2O$ at 45° C.

The result of the oxidation in water is particularly interesting because the reaction is highly ecocompatible and with a low environmental impact.

The reaction has been repeated even in condition of stage transfer using pentane, heptane and other similar solvents.

Besides two other kinds of rhenium heterogeneous catalysts have been prepared, based on the Methylrhenium Trioxide heterogenization (MTO) on poly(4-vinylpyridine) and polystyrene, according to the literature (R. Saladino, et al. "Preparation and Structural Characterization of Polymer-supported Methylrhenium Trioxide Systems as Efficient and Selective Catalysts for the Epoxidation of Olefins" *J. Org. Chem.*, 2002, 67, 1323-1332).

i) Preparation of the Poles Catalysts (4-vinylpyridine)/MTO 77 mg (0.3 mmol) of MTO were added to a resin suspension of 600 mg [poly(4-vinylpyridine) 2% or 25% cross-linked with divinylbenzene] in 4 ml of ethanol and the mixture was stirred for about 1 h using a magnetic stirrer.

The solvent was removed by filtration, and the solid residue was successively washed with ethyl acetate and dried up under high vacuum. At any rate, the added MTO was completely bound to the support as confirmed from the spectroscopic analysis on the residue obtained after evaporation of the organic stage used for the catalyst washing. The so obtained catalysts, hereinafter referred to as PV2M [catalyst poly(4-vinylpyridine) 2%/MTO] have been characterized by Scanning Electron Microscope (SEM) and by x-ray diffraction with the low energy technique. The degree of support cross-linking controls the shape of the catalyst's particles. A low value of the cross-linking degree (2%) produces irregular shaped particles, but with the highest value (25%) it produces perfectly spherical particles with a medium diameter of about 500 μm. Rhenium atom has a distorted octahedral coordination and two pyridine ligands in a cis configuration. The presence of a double anchoring site of metal to the support is the indication of a stable system as it was then confirmed by the oxidation assays. A similar procedure has been carried out using poly(4-vinylpyridine) 2%-N-oxide as support. The corresponding catalyst, in which MTO is coordinated to the resin by oxygen and not a nitrogen atom, will be indicated with PV2NM.

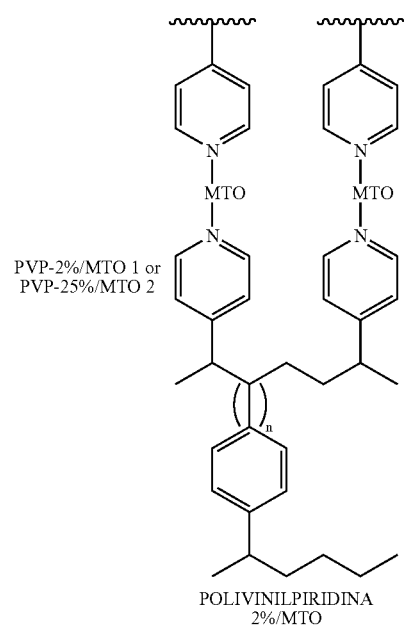

PVP-2%/MTO 1 or
PVP-25%/MTO 2

POLIVINILPIRIDINA
2%/MTO

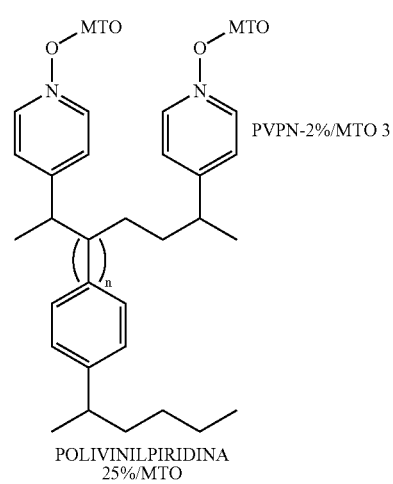

PVPN-2%/MTO 3

POLIVINILPIRIDINA
25%/MTO ii) Preparation of MTO Microencapsulated Catalyst 77 mg (0.3 mmol) of MTO were added to a suspension of 600 mg of polystyrene in 4 ml of tetrahydrofuran (THF) and the mixture was stirred for about 1 h using a magnetic stirrer. The reaction mixture was successively added with n-hexane and the solid residue was filtered and washed by ethyl acetate. Even in this case the added MTO was completely bound to the support as confirmed by the spectroscopic analysis of the residue after evaporation of the organic phase used to wash the catalyst. The analysis by Scanning Electron Microscope (SEM) shows the formation of perfectly spherical microcapsules of about 50 μm average diameter. The corresponding catalyst, where MTO is physically trapped within the microcapsule, will be hereinafter referred to as PS2M.

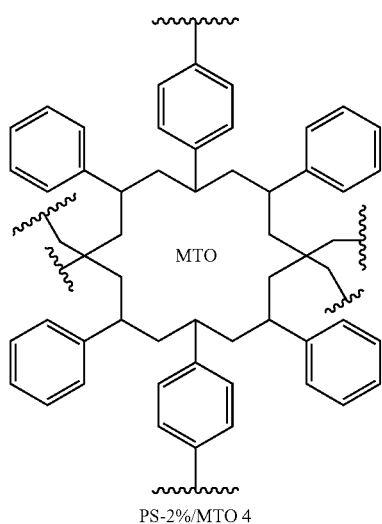

PS-2%/MTO 4

Tyrosol Oxidative Reactions

All heterogeneous catalysts are used for the innovative transformation of Tyrosol to Hydroxytyrosol. Some examples are described below.

Oxidative reactions have been performed using Tyrosol from purification of the oil mill wastewaters. Reactions were performed with a Tyrosol concentration of 100 mg/ml in ethanol at 40° C. with all heterogeneous catalysts described before, using a small excess of hydrogen peroxide ($H_2O_2$, 2 equivalents) at 30% in water solution as primary oxidant. Initially a loading factor (loading parameter corresponding to mmol of active MTO per resin gram) equal to 0.5 (Scheme 3) was chosen for catalysts.

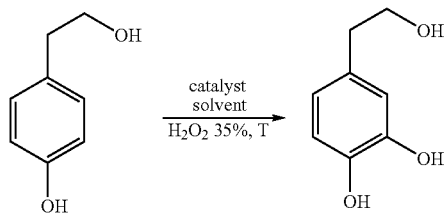

Scheme 3

This value is particularly low because, in industrial applications, values of the loading factor between 1.0 and 10 are normally used. Reactions were performed for 24 h. At the end, they have been treated with two alternative methods.

Method A: the reaction mixture was diluted with ethyl acetate and a catalytic amount of $MnO_2$ was added to destroy the possible oxidant excess. $MnO_2$ was filtered away and solvent evaporated obtaining a raw reaction containing mainly Tyrosol (un-reacted) and Hydroxytyrosol.

Method B: (ascorbic acid method): at the end of the reaction, the mixture was diluted with 3 volumes of cold methanol and the same quantity in weight (as to the primary Tyrosol) of ascorbic acid (Vitamin C) was added. After 15 minutes, 4 volumes of water were added, which contain a high percentage of ascorbic acid, identical to the previous one. Stirring must be continued for 30 minutes and then repeated extractions with ethyl acetate must be carried out. After one night in the fridge the combined organic phases were stable in the Hydroxytyrosol contents even without being separated from the residual water by sodium sulphate. The method B is more efficient and it has been used to continue experimentation. The reaction crude products have been purified by flash-chromatography on silica, using the ethyl acetate/n-hexane mixture, or on magnesium silicate Florisil® absorbant. In the latter case, the adsorbent Florisil® has been used with a loading of 5% (example: for 1 g of mixture to separate 20 g of Florisil® are needed, which are like about 40 ml called Bed Volume—BV) on a so characterized column:

$D_i$=BV/10 cm

H=BV/p cm

Flow rate=BV/2 ml/min or more

The mixture Hydroxytyrosol/Tyrosol was dispersed in 4 BV of a 1:1 Ether/Hexane mixture. The column was eluted with a maximum of 20 BV of the same mixture, completely extracting the pure Tyrosol from the mixture of the column. The column was eluted with a maximum of 15 BV of Ether, which extract pure Hydroxytyrosol contained in the column. The results of this sperimentation are shown in FIG. 4.

Figure 4:
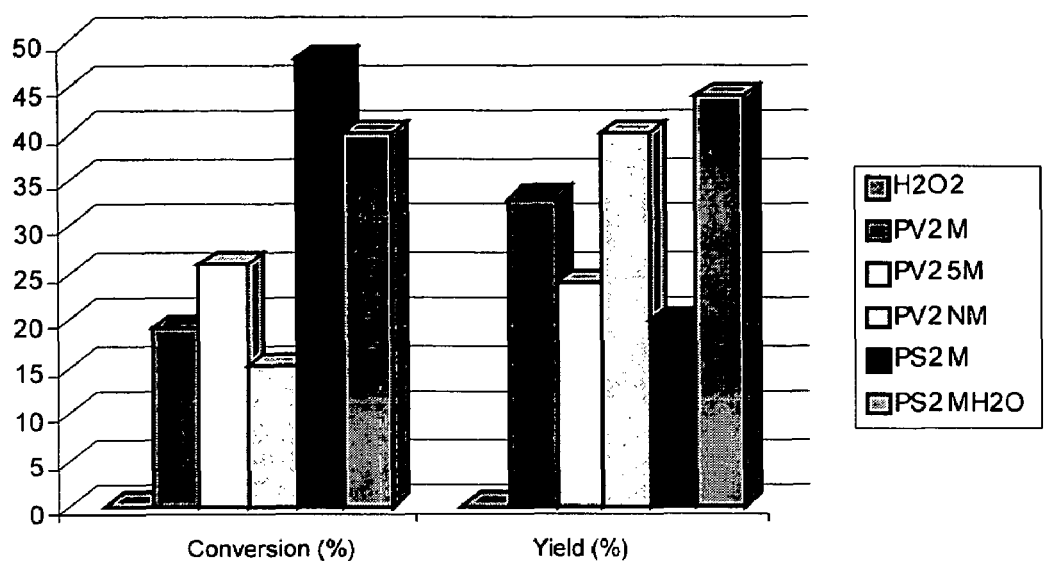
FIG. 4 is a bar chart showing the effectiveness of various catalysts used to oxidize Tyrosol to Hydroxytyrosol.

From the histogram of FIG. 4, it is observed that several rhenium catalysts are able to successfully oxidize Tyrosol to Hydroxytyrosol. In the reaction performed in ethanol, the microencapsulated catalyst PS2M gives the highest yield of Hydroxytyrosol equal to 40%. The water is an optimal solvent in the reaction with catalyst PV2M. In fact, in these last experimental conditions, a substrate conversion equal to 40% and a Hydroxytyrosol yield of 43% is observed. The rhenium heterogeneous catalysts are stable systems and can be easily recovered from the reaction system to be used in more sequential transformation reactions. Table 4 reports data about Tyrosol conversion after many transformation cycles performed with PV2M and PV25M systems. Catalysts remain stable systems for at least 10 oxidative cycles.

TABLE 4

| | Data about recovery and use of catalysts expressed as conversion of Tyrosol to Hydroxytyrosol | | | | | | | | | |
|---|---|---|---|---|---|---|---|---|---|---|
| | Cycle | | | | | | | | | |
| Catalyst | 1 | 2 | 3 | 4 | 5 | 6 | 7 | 8 | 9 | 10 |
| PV2M | 18 | 20 | 19 | 17 | 18 | 21 | 20 | 20 | 18 | 18 |
| PV25M | 27 | 30 | 28 | 27 | 29 | 30 | 27 | 28 | 26 | 25 |

EXAMPLE 3

Applicative Use of One of the Purified and/or Semi-Synthesized (Hydroxytyrosol) Compound Obtained by the Described Process Hydroxytyrosol, obtained with the innovative process here described, has been used on endothelial cell cultures obtained from human umbilical veins endothelium (HUVECs) sampled and stored as described by Carluccio and co-workers [Carluccio M. A., et al.; "Olive oil and red wine antioxidant polyphenols inhibit endothelial activation: antiatherogenic properties of Mediterranean diet phytochemicals"; *Arteroscler. Thromb. Vasc. Biol.* 23, 622-9 (2003)], and on a monocytic cell line U937 obtained from the American Type Culture Collection, grown in RPMI1640 containing 10% FCS.

To evaluate the inhibition of cell growth, HUVEC and U937 monocytes proliferation was followed counting vital cells using the trypan blue exclusion method and using the MTT (3-[4,5-dimethyl (thiazol-2-yl)]-3,3diphenyltetrazolium-bromide) assay as described by Fabiani and co-workers [Fabiani R., et al.; "Cancer chemoprevention by Hydroxytyrosol isolated from virgin olive oil through G1 cell cycle arrest and apoptosis"; *Eur. J. Cancer Prev. Aug;* 11(4): 351-8 (2002)].

The apoptosis has been evaluated using Annexin V-FITC Kit (Sigma™) according to instructions and analysed by FACS. Cell cultures ($10^5$/ml) have been treated with Hydroxytyrosol, obtained by the above-mentioned industrial process, for 48 hours before apoptosis essays.

Hydroxytyrosol (0-100 μmoles/l) has been studied for its effects on cell growth and the apoptosis induction in monocytic cells (U937), in HUVEC and in transformed human endothelial cells (EVC 304).

At the concentration of 100 μmoles/l for 48 hours, Hydroxytyrosol produced with the above-mentioned industrial process completely inhibits cell proliferation in U937, but at 30 μmoles/l an inhibition of the cell growth of about 50% is noticed. At these concentrations there are no significant variations in the HUVEC and ECV304 proliferation.

From this, it can be seen that, at in vivo concentrations, Hydroxytyrosol produced with the above-mentioned industrial process inhibits the proliferation and it induces the apoptosis in monocytic cells, but not in the endothelial ones.

EXAMPLE 4

Applicative Use of One of the Purified (Hydroxytyrosol) Compound Obtained by the Described Process, in Dermocosmetic and Pharmaceutical Preparations for Skin Depigmentation and Lightening The different fractions and compounds Tyrosol, Hydroxytyrosol, etc, obtained by the described process, were used for the formulation of products for topical use to oppose melanogenesis and to induce lightening and depigmentation of the user's derma.

Some examples of formulations are reported below:

Dermocosmetic Preparation as "Milk"

| Ingredient | % |
| --- | --- |
| Cetyl stearylic alcohol | 4.00 |
| Glyceryl Monostearate S/E (self-emulsioning) | 5.00 |
| Vaseline oil | 10.00 |
| Siliconic fluid | 2.00 |
| Propylene glycol | 10.00 |
| Methyl Para Hydroxybenzoate | 0.20 |
| Propyl Para Hydroxybenzoate | 0.20 |
| Aroma | 0.25 |
| Tyrosol (*) | 10.00 |
| Citric acid (corrector to pH 4-5) | q.b. |
| Water | q.b. |

(*) The described formulation is typical but this ingredient percentage can be varied from 0.0001% to 50.00%

Dermocosmetic Preparation as "Gel"

| Ingredients | % |
| --- | --- |
| Propylene glycol | 88.90 |
| EDTA disodium salt | 0.05 |
| Carbomer | 0.95 |
| Sodium hydroxide (30% Solution) | 0.10 |
| Tyrosol (*) | 10.00 |

(*) The described formulation is typical but this ingredient percentage can be varied from 0.0001% to 50.00%

Dermocosmetic Preparation as "Cream"

| Ingredient | % |
| --- | --- |
| Glyceryl Monostearate | 8.00 |
| Diethylene Glycol Palmito Stearate | 6.00 |
| Diethylene Glycol Stearate | 6.00 |
| Glycerin | 3.00 |
| Vaselin oil | 1.50 |
| Siliconic fluid | 0.50 |
| Aroma | 0.25 |
| Butyl Para Hydroxybenzoate | 0.40 |
| Methyl Para Hydroxybenzoate | 0.10 |
| Propylene glycol | 6.00 |
| Tyrosol (*) | 10.00 |
| Water | q.b. |

(*) The described formulation is typical but this ingredient percentage can be varied from 0.0001% to 50.00%

Figure 5:
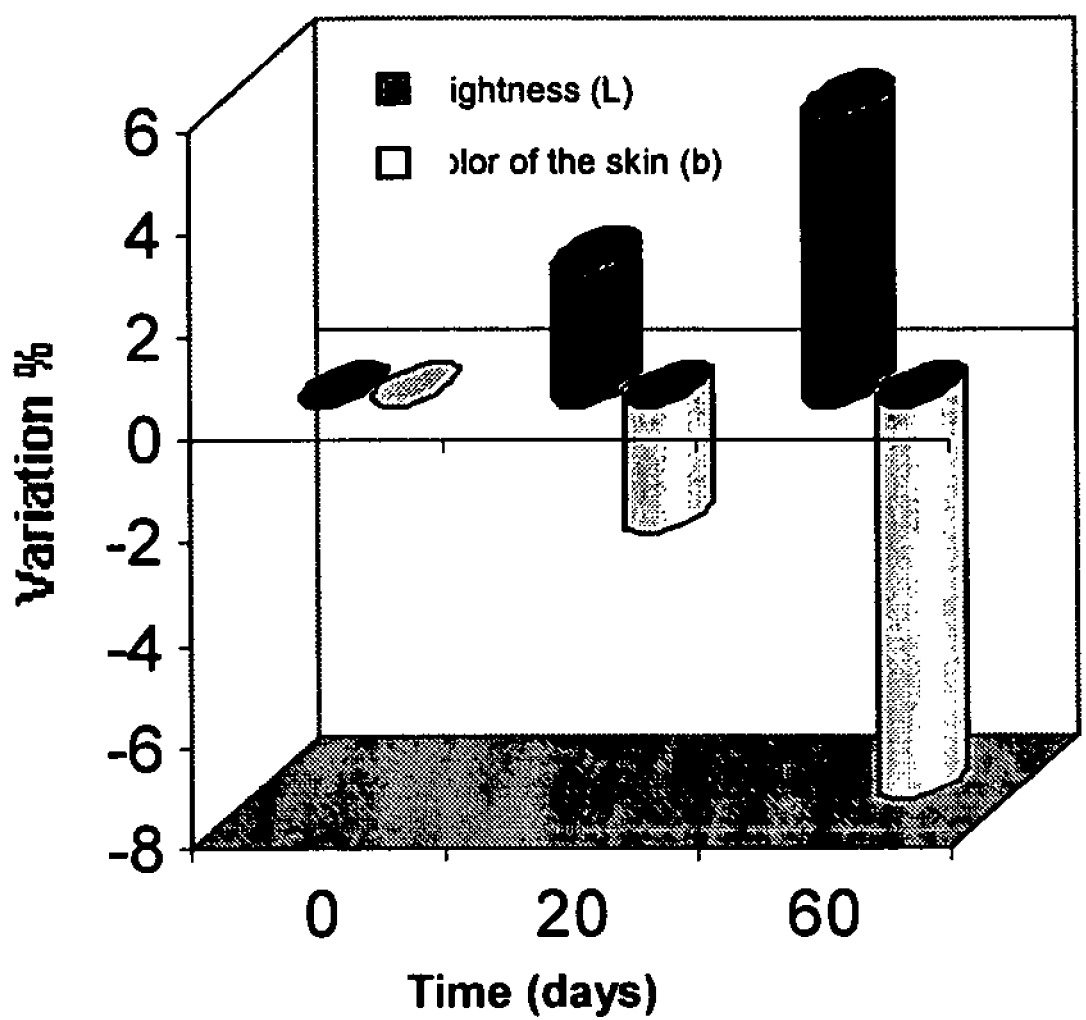
FIG. 5 is a diagram showing the percent variation in color and luminosity, with time, of the lotion of the present invention compared to a placebo.

The first data obtained using these preparations are evidenced in the following graphic and demonstrate that, after a 20 days treatment, in 50% of treated subjects there is between 2 and 3% skin lightening increase and about 2.5% colour decrease. After 60 days 25% of treated subjects evidenced about 6% skin lightening increase and about 8% colour decrease. FIG. 5 shows data about the preparation as "lotion" compared to a placebo.

No variation of the parameters studied on skin has been found after the application of the placebo formulation for each 60 days treatment. This result shows how the placebo formulation components do not have a positive action in reducing skin pigmentation.

EXAMPLE 5

Applicative Use of the Obtained Fractions and of One of the Purified Substances (Tyrosol, Hydroxytyrosol, etc.) According to the Process Described for Nutraceutical and Dietary Formulations The different fractions and Tyrosol, Hydroxytyrosol, etc., obtained by the described process, have been used for the formulation of nutraceutical and dietary product.

Here below some examples of the obtained formulations are shown:

Preparation as "Drink Based on Water (1)"

| Ingredient | % |
| --- | --- |
| Hydroxytyrosol (*) | 0.0077 |
| Tyrosol (*) | 0.0069 |
| Gallic acid (3,4,5-Trihydroxybenzoic acid) (*) | 0.0085 |
| Oleuropein (*) | 0.0270 |
| Acesulfam K | 0.0125 |
| Potassium Sorbate | 0.0550 |
| Sodium benzoate | 0.0550 |
| Ascorbic acid | 0.0833 |
| Sorbitol 70% solution | 0.1667 |
| MALTISORB ® "P200" | 0.1667 |
| Citric acid mono hydrate | 0.0833 |
| Vegetable dietary fiber | 10.580 |
| Aroma | 0.3833 |
| Microfiltered water | q.b. |

(*) The described formulation is typical, but this ingredient percentage can be varied from 0.00001% to 20.00%.

Preparation as "Drink Based on Water (2)"

| Ingredient | % |
| --- | --- |
| Hydroxytyrosol (*) | 0.0077 |
| Tyrosol (*) | 0.0069 |
| Gallic acid (3,4,5-Trihydroxybenzoic acid) (*) | 0.0085 |
| Oleuropein (*) | 0.0270 |
| Acesulfam K | 0.0125 |
| Potassium Sorbate | 0.0550 |
| Sodium benzoate | 0.0550 |
| Ascorbic acid | 0.0833 |
| MALTISORB ® "P200" | 0.1667 |
| Citric acid mono hydrate | 0.0833 |
| Vegetable dietary fiber | 10.580 |
| Aroma | 0.3833 |
| Microfiltered water | q.b. |

(*) The described formulation is typical, but this ingredient percentage can be varied from 0.00001% to 20.00%.

Preparation as "Drink Based on Water (3)"

| Ingredient | % |
| --- | --- |
| Hydroxytyrosol (*) | 0.007 |
| Tyrosol (*) | 0.0069 |
| Gallic acid (3,4,5-Trihydroxybenzoic acid) (*) | 0.0085 |
| Oleuropein (*) | 0.0270 |
| Processed NF fraction (*) | 0.9320 |
| Processed UF2 fraction (*) | 1.5870 |
| Glucidex | 6.0000 |
| Potassium Sorbate | 0.0550 |
| Sodium benzoate | 0.0550 |
| Ascorbic acid | 0.0833 |
| Citric acid mono hydrate | 0.0833 |
| Aromas | 0.3833 |
| Microfiltered water | q.b. |

(*) The described formulation is typical, but this ingredient percentage can be varied from 0.00001% to 20.00%.

Preparation as "Drink Based on Water (4)"

| Ingredient | % |
| --- | --- |
| Hydroxytyrosol (*) | 0.0007 |
| Tyrosol (*) | 0.0007 |
| Gallic acid (3,4,5-Trihydroxybenzoic acid) (*) | 0.0008 |
| Processed NF fraction (*) | 0.0093 |
| Processed UF2 fraction (*) | 0.0159 |
| Ascorbic acid | 0.0833 |
| Microfiltered water | q.b. |

(*) The described formulation is typical, but this ingredient percentage can be varied from 0.00001% to 20.00%.

Preparation as "Drink Based on Water (5)"

| Ingredient | % |
| --- | --- |
| Hydroxytyrosol (*) | 0.0007 |
| Tyrosol (*) | 0.0007 |
| Gallic acid (3,4,5-Trihydroxybenzoic acid) (*) | 0.0008 |
| Processed NF fraction (*) | 0.0093 |
| Processed UF2 fraction (*) | 0.0159 |
| Sodium acid carbonate | 0.1694 |
| Ascorbic acid | 0.0833 |
| Microfiltered water | q.b. |

(*) The described formulation is typical, but this ingredient percentage can be varied from 0.00001% to 20.00%.

Preparation as "Drink Based on Water (6)"

| Ingredient | % |
| --- | --- |
| Hydroxytyrosol (*) | 0.0007 |
| Tyrosol (*) | 0.0007 |
| Gallic acid (3,4,5-Trihydroxybenzoic acid) (*) | 0.0008 |
| Processed NF fraction (*) | 0.0093 |
| Processed UF2 fraction (*) | 0.0159 |
| Sodium chloride | 0.0778 |
| Sodium citrate | 0.1965 |
| Potassium Phosphate Monobasic | 0.0419 |
| Magnesium carbonate | 0.0175 |
| Glucidex | 6.0000 |
| Citric acid (pH adjuster) | q.b. |
| Microfiltered water | q.b. |

(*) The described formulation is typical, but this ingredient percentage can be varied from 0.00001% to 20.00%.

The invention claimed is:

1. A process to treat the oil mill wastewaters (OMW) and especially for the preparation of Tyrosol and/or Hydroxytyrosol, which consists of:
   a) Rough Filtration (RF), Microfiltration (MF), Ultrafiltration (UF), Nanofiltration (NF) and Reverse Osmosis (RO) of the OMW;
   b) Chromatographic separation of Tyrosol, Hydroxytyrosol and other phenolic compounds from the concentrated RO;

c) Oxidation of the so obtained Tyrosol to Hydroxytyrosol in the presence of methylrhenium trioxide and of hydrogen peroxide in a protic solvent;

d) Concentration and pulverization of the high molecular weight portion with the recovery of water and compounds with a high added value.

2. A process according to claim 1 allowing to recover at least 85% of detoxified water according to the control parameters defined by the law in force about the agricultural and civil re-use.

3. A process according to claim 1 wherein in the step a) the concentration ratio (fed/extract) is higher than 8.

4. A process according to claim 1 wherein in the step a) the phases of Ultrafiltration, Nanofiltration and Inverse Osmosis are carried out at neutral or alkaline pH.

5. A process according to claim 1. wherein in the step a) the temperature is lower than 60° C.

6. A process according to claim 1 wherein in the steps from a) to d) the process can also be performed in controlled and inert atmosphere.

7. A process according to claim 1 wherein step c) is carried out in homogeneous phase using the catalyst methyl rhenium trioxide bound to a polymeric matrix in protic solvents.

8. A process according to claim 1 wherein step c) is carried out in heterogeneous phase using the catalyst methyl rhenium trioxide bound to a polymeric matrix in protic solvents.

9. A process according to claim 7 wherein the polymeric matrix consists of polyvinylpyridine or polystyrene.

10. A process according to claim 7 wherein in the step c) the solvent is selected from water, ethanol or acetic acid.

11. A process according to claim 1 wherein the chromatographic separation of the OMW components is carried out on a stationary phase consisting of a divinylbenzene/ N-vinyl 2-pyrrolidone co-polymer.

12. A process according to claim 2 wherein in the step a) the temperature is lower than 60° C.

13. A process according to claim 2 wherein in the steps from a) to d) the process can also be performed in controlled and inert atmosphere.

14. A process according to claim 8 wherein the polymeric matrix consists of polyvinylpyridine or polystyrene.

15. A process according to claim 8 wherein in the step c) the solvent is selected from water, ethanol or acetic acid.

* * * * *